US010638954B2

(12) United States Patent
Gliner et al.

(10) Patent No.: US 10,638,954 B2
(45) Date of Patent: May 5, 2020

(54) SURFACE REGISTRATION OF A CT IMAGE WITH A MAGNETIC TRACKING SYSTEM

(71) Applicant: Biosense Webster (Israel) Ltd., Yokneam (IL)

(72) Inventors: Vadim Gliner, Haifa (IL); Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 965 days.

(21) Appl. No.: 15/210,432

(22) Filed: Jul. 14, 2016

(65) Prior Publication Data

US 2017/0020411 A1    Jan. 26, 2017

Related U.S. Application Data

(60) Provisional application No. 62/195,905, filed on Jul. 23, 2015.

(51) Int. Cl.
| | |
|---|---|
| *A61B 5/00* | (2006.01) |
| *A61B 5/06* | (2006.01) |
| *A61B 6/00* | (2006.01) |
| *A61B 6/03* | (2006.01) |

(Continued)

(52) U.S. Cl.
CPC ............ *A61B 5/066* (2013.01); *A61B 5/0035* (2013.01); *A61B 5/062* (2013.01); *A61B 5/068* (2013.01); *A61B 5/6814* (2013.01); *A61B 5/6843* (2013.01); *A61B 6/00* (2013.01); *A61B 6/032* (2013.01); *A61B 6/5247* (2013.01);

(Continued)

(58) Field of Classification Search
CPC ..................................................... A61B 5/066
See application file for complete search history.

(56) References Cited

U.S. PATENT DOCUMENTS

| | | | | |
|---|---|---|---|---|
| 5,348,008 A | * | 9/1994 | Bornn ................. | A61B 5/0006 600/301 |
| 7,072,707 B2 | | 7/2006 | Galloway, Jr. et al. | |

(Continued)

FOREIGN PATENT DOCUMENTS

WO    WO 2002/000093 A2    1/2002

OTHER PUBLICATIONS

European Search Report dated Dec. 9, 2016 from corresponding European Patent Application No. 16180698.9.

*Primary Examiner* — Rochelle D Turchen

(74) *Attorney, Agent, or Firm* — Todd J. Burns

(57) ABSTRACT

Apparatus, including a magnetic tracking system, which generates a magnetic field near a living subject's body, and a probe, having a distal end that can contact registration points on a surface of the body. The probe has a contact sensor, located within the distal end, that outputs first signals indicative of a quality of the contact between the distal end with the registration points. Located within the distal end is a magnetic detector that outputs second signals that are indicative of respective positions of the registration points in a coordinate frame of the magnetic tracking system. A processor receives a tomographic image of the subject, and verifies, based on the quality of the contact indicated by the first signals, that the registration points are valid, and registers the tomographic image in the coordinate frame of the magnetic tracking system using the positions of the valid registration points.

10 Claims, 3 Drawing Sheets

(51) Int. Cl.
*A61B 90/00* (2016.01)
*A61B 34/20* (2016.01)
(52) U.S. Cl.
CPC . *A61B 2034/2051* (2016.02); *A61B 2090/065* (2016.02); *A61B 2090/3762* (2016.02)

(56) References Cited

U.S. PATENT DOCUMENTS

| | | | |
|---|---|---|---|
| 8,031,916 B2* | 10/2011 | Abiko | G06K 9/00919 |
| | | | 283/68 |
| 8,636,519 B2 | 1/2014 | Schwartz et al. | |
| 9,019,262 B2 | 4/2015 | Ma et al. | |
| 2007/0276234 A1 | 11/2007 | Shahidi | |
| 2007/0299334 A1 | 12/2007 | Vilsmeier | |
| 2009/0299174 A1 | 12/2009 | Wright et al. | |
| 2010/0063387 A1* | 3/2010 | Timinger | A61B 90/36 |
| | | | 600/426 |
| 2016/0008058 A1* | 1/2016 | Hu | A61M 25/0147 |
| | | | 606/21 |

* cited by examiner

SURFACE REGISTRATION OF A CT IMAGE WITH A MAGNETIC TRACKING SYSTEM

CROSS-REFERENCE TO RELATED APPLICATION

This application claims the benefit of U.S. Provisional Patent Application 62/195,905, filed Jul. 23, 2015, which is incorporated herein by reference.

FIELD OF THE INVENTION

The present invention relates generally to registration of different modalities used in a medical procedure, and specifically to registration of an image of a subject with a system configured to track an instrument within the subject.

BACKGROUND OF THE INVENTION

In order to perform registration of a magnetic tracking system with an image of a subject, in prior art systems a probe that is tracked by the magnetic tracking system is positioned at pre-determined features of the subject. The feature locations of the probe as determined by the tracking system are correlated with the feature locations determined from an image of the subject, typically a computerized tomography (CT) image, and the correlation is used to register the image with the tracking system. However, the positioning of the probe at the pre-determined features is typically not exact, and may differ by more than 1 mm from the correct position. For example, at a given feature the probe may be pushed against the subject, depressing the skin at that location, leading to an inaccurate registration. Alternatively, at another location, the probe may not even contact the feature, again leading to an inaccurate registration.

PCT application WO2002/000093A2, to Yagel, whose disclosure is incorporated herein by reference, describes a system for registration of target object images to stored image data. Two-dimensional images are registered with both a reference coordinate system and with a previously acquired three-dimensional image of the target to provide a coordinate transformation from the reference coordinate system to the target.

US Patent application 2007/0276234, to Shahidi, whose disclosure is incorporated herein by reference, describes a method which is claimed to assist a user in guiding a medical instrument to a subsurface target site in a patient. The method is stated to generate at least one intraoperative ultrasonic image and to indicate a target site on the ultrasonic image(s).

U.S. Pat. No. 8,636,519 to Schwartz, et al., whose disclosure is incorporated herein by reference, describes a mockup probe, having a distal end and a proximal end adapted to be held by a human operator. A mockup patient, simulating an actual patient, has an aperture allowing penetration of the distal end of the mockup probe into the mockup patient. A force generator, is coupled to the mockup probe so as to apply a force to the proximal end that can be felt by the human operator, and a controller is configured to track the distal end.

U.S. Pat. No. 7,072,707 to Galloway, Jr., et al., whose disclosure is incorporated herein by reference, describes a method for collecting and processing physical space data for use while performing image-guided surgery. Physical space data is stated to be collected by probing physical surface points of surgically exposed tissue. The physical space data provides 3D coordinates for each of the physical surface points. Based on the physical space data collected, point-based registrations used to indicate surgical position in both image space and physical space are determined.

U.S. Pat. No. 9,019,262 to Ma, et al., whose disclosure is incorporated herein by reference, describes a method for transforming a displayed three-dimensional image corresponding to a position and orientation of a field of view of an imaging probe. A three dimensional image of a tissue in a first co-ordinate space can be displayed. A field of view of the imaging probe in a second co-ordinate space can be configured, and the first and second co-ordinate spaces can be co-registered.

US Patent application 2009/0299174, to Nelson, et al., whose disclosure is incorporated herein by reference, describes a method for tracking an instrument in a human patient. The instrument has an elongated body, such as an elongated flexible member, having a distal section configured to be passed through a vessel or other passageway in a human. The instrument can further include a lumen through the distal section and a magnetic marker having a transponder at the distal section.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides apparatus, including:

a magnetic tracking system, which is configured to generate a magnetic field in a vicinity of a body of a living subject;

a probe, having a distal end configured to be brought into contact with one or more registration points on a surface of the body, and including:

a contact sensor, located within the distal end and configured to output first signals indicative of a quality of the contact between the distal end with the one or more registration points; and a magnetic detector, located within the distal end and configured to output second signals in response to the magnetic field that are indicative of respective positions of the one or more respective registration points in a coordinate frame of the magnetic tracking system; and a processor configured to receive a tomographic image of the subject, and to verify, based on the quality of the contact indicated by the first signals, that the one or more registration points are valid, and to register the tomographic image in the coordinate frame of the magnetic tracking system using the positions of the one or more registration points that were verified to be valid.

In one embodiment the contact sensor consists of an electrode, and verifying that the one or more registration points are valid includes verifying that an impedance measured by the electrode on contact with each of the registration points lies within a predetermined range. The predetermined range may be 20 k$\Omega$-40 k$\Omega$ when the impedance is measured at 20 kHz. Alternatively or additionally, the predetermined range may be evaluated in response to a position of a grounding element on the surface of the body, and in response to a degree of contact of the grounding element with the surface.

In a disclosed embodiment the apparatus includes a handle connected to the probe so as to form a rigid probe assembly.

In a further disclosed embodiment the one or more registration points are selected to be visible to a naked eye of a user of the probe.

In a yet further disclosed embodiment the one or more registration points are selected to be immobile on the surface of the body.

Alternatively, the contact sensor consists of a force sensor, and verifying that one or more registration points are valid includes verifying that a force measured by the force sensor on contact with each registration point lies within a predetermined range. The predetermined range may be 2 gm-8 gm. Alternatively or additionally, the predetermined range is evaluated in response to a user of the probe contacting preselected points on the surface of the body.

There is further provided, according to an embodiment of the present invention, a method, including:

generating, with a magnetic tracking system, a magnetic field in a vicinity of a body of a living subject;

bringing a distal end of a probe into contact with one or more registration points on a surface of the body, the probe comprising:

a contact sensor, located within the distal end and configured to output first signals indicative of a quality of the contact between the distal end with the one or more registration points, and a magnetic detector, located within the distal end and configured to output second signals in response to the magnetic field that are indicative of respective positions of the one or more respective registration points in a coordinate frame of the magnetic tracking system;

receiving a tomographic image of the subject;

verifying, based on the quality of the contact indicated by the first signals, that the one or more registration points are valid; and registering the tomographic image in the coordinate frame of the magnetic tracking system using the positions of the one or more registration points that were verified to be valid.

The present disclosure will be more fully understood from the following detailed description of the embodiments thereof, taken together with the drawings, in which:

DETAILED DESCRIPTION OF EMBODIMENTS

Overview

Embodiments of the present invention make the process of registering a magnetic tracking system with the image of a subject more exact than prior art registration systems. A contact sensor is incorporated into a probe that is tracked by the magnetic tracking system, and the sensor provides a numerical reading of a "degree" or quality of contact of the probe with the skin of a subject at features of the subject being used for registration with the image. (Locations of the features are also determined in the image.) In one embodiment the sensor comprises an electrode, and an impedance measured by the electrode is used to quantify the degree of contact, and give an indication that the contact is valid. In an alternative embodiment the sensor comprises a force sensor, and the value of the force measured is used to indicate that the contact is valid.

In a disclosed embodiment registration apparatus comprises a magnetic tracking system, which is configured to generate a magnetic field in a vicinity of a body of a living subject, typically a human subject. A user of the apparatus brings a distal end of a probe into contact with one or more registration points on a surface of the body. A contact sensor is located in the distal end, and outputs first signals indicative of a quality of the contact between the distal end with the one or more registration points. A magnetic detector is also located in the distal end, and outputs second signals in response to the magnetic field that are indicative of respective positions of the one or more respective registration points in a coordinate frame of the magnetic tracking system.

The disclosed embodiment also comprises a processor which receives a tomographic image of the subject. The processor verifies, based on the quality of the contact indicated by the first signals, that the one or more registration points are valid. The processor then registers the tomographic image in the coordinate frame of the magnetic tracking system using the positions of the one or more registration points that were verified to be valid.

Detailed Description

Figure 1:
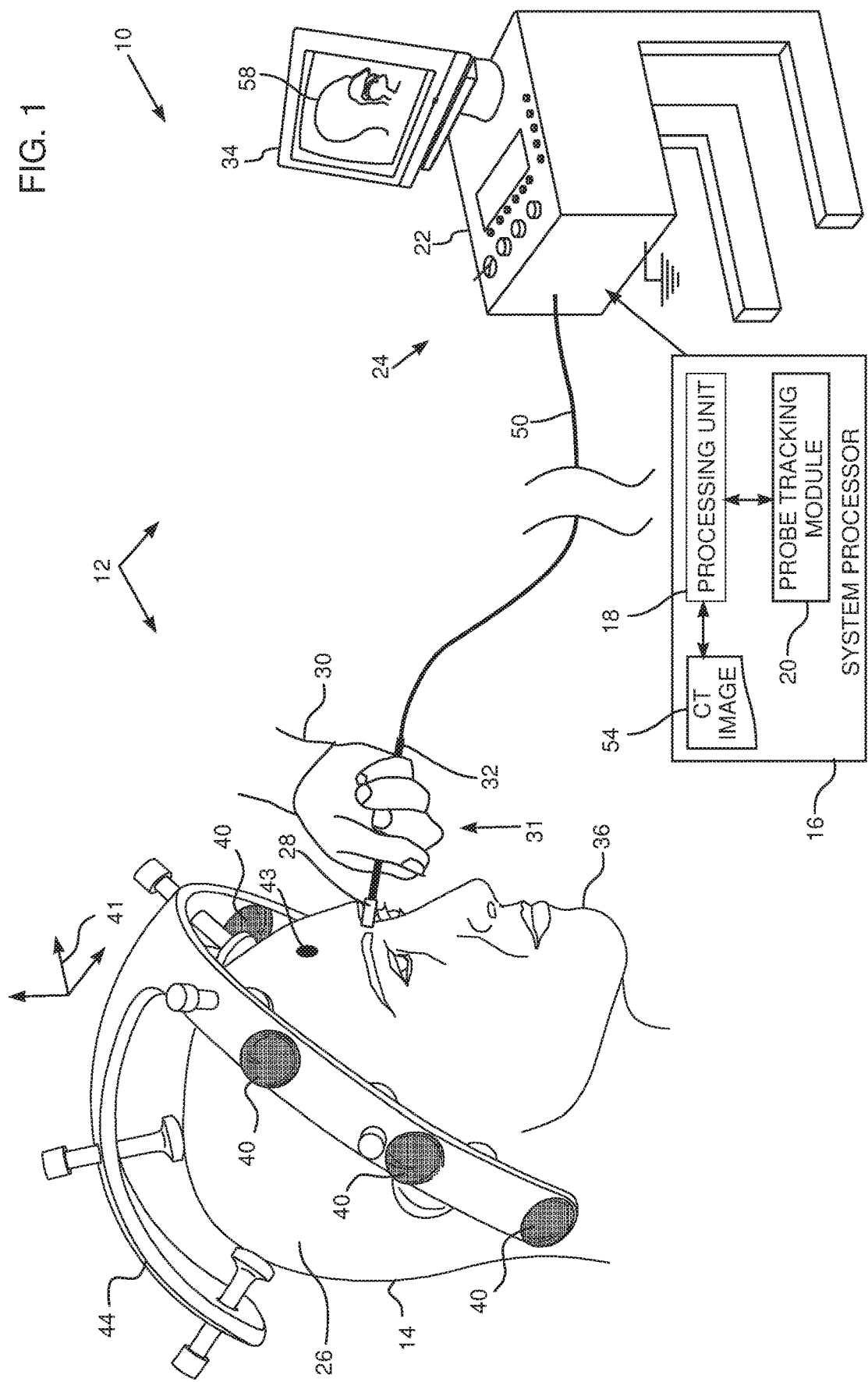
FIG. 1 is a schematic diagram of a surface registration system, according to an embodiment of the present invention.
Figure 2A:
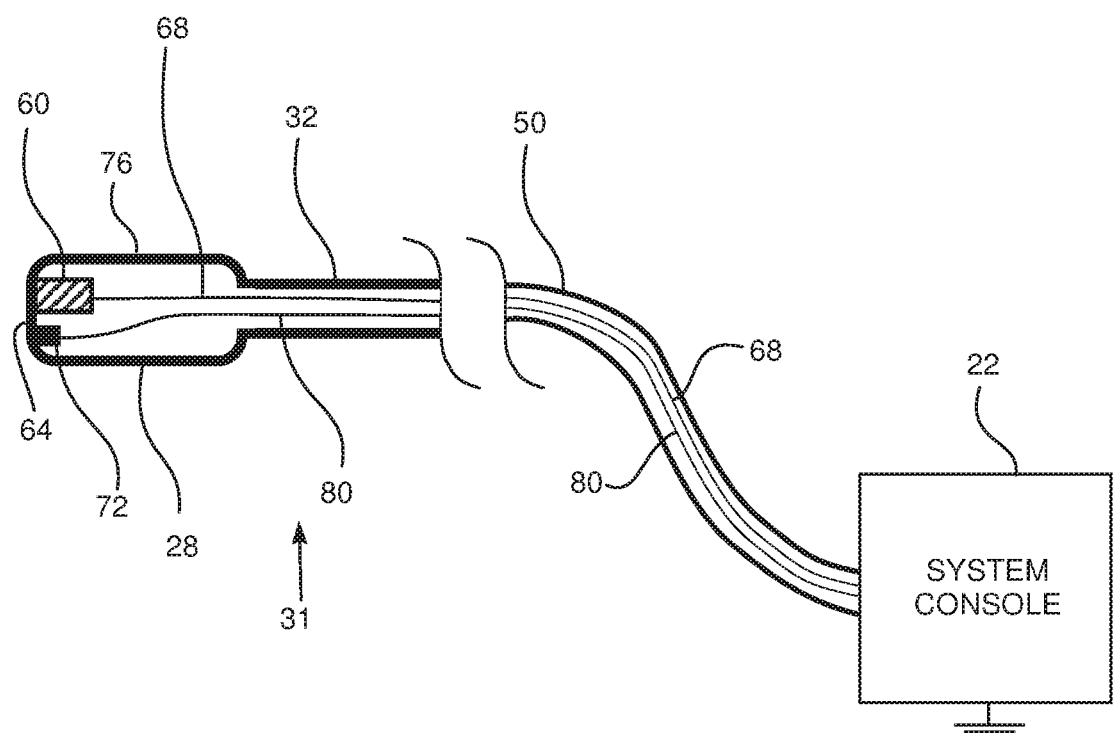
FIGS. 2A and 2B are schematic diagrams of probes used in the system, according to embodiments of the present invention.
Figure 2B:
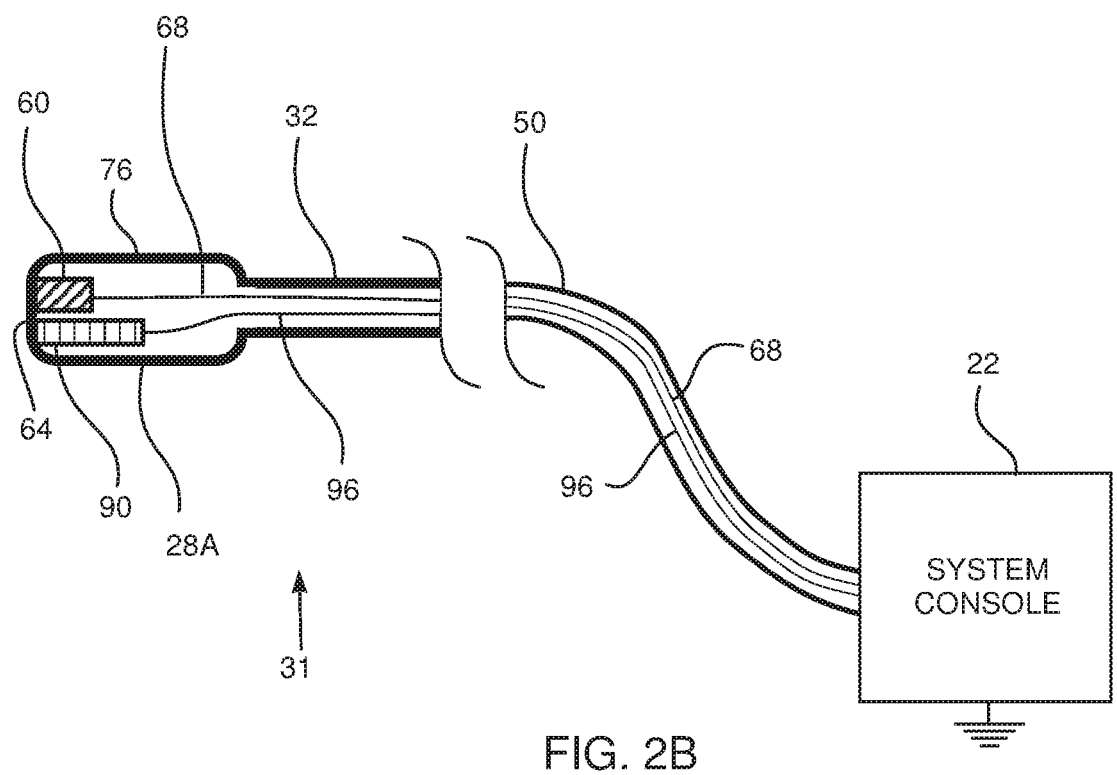
Figure 3:
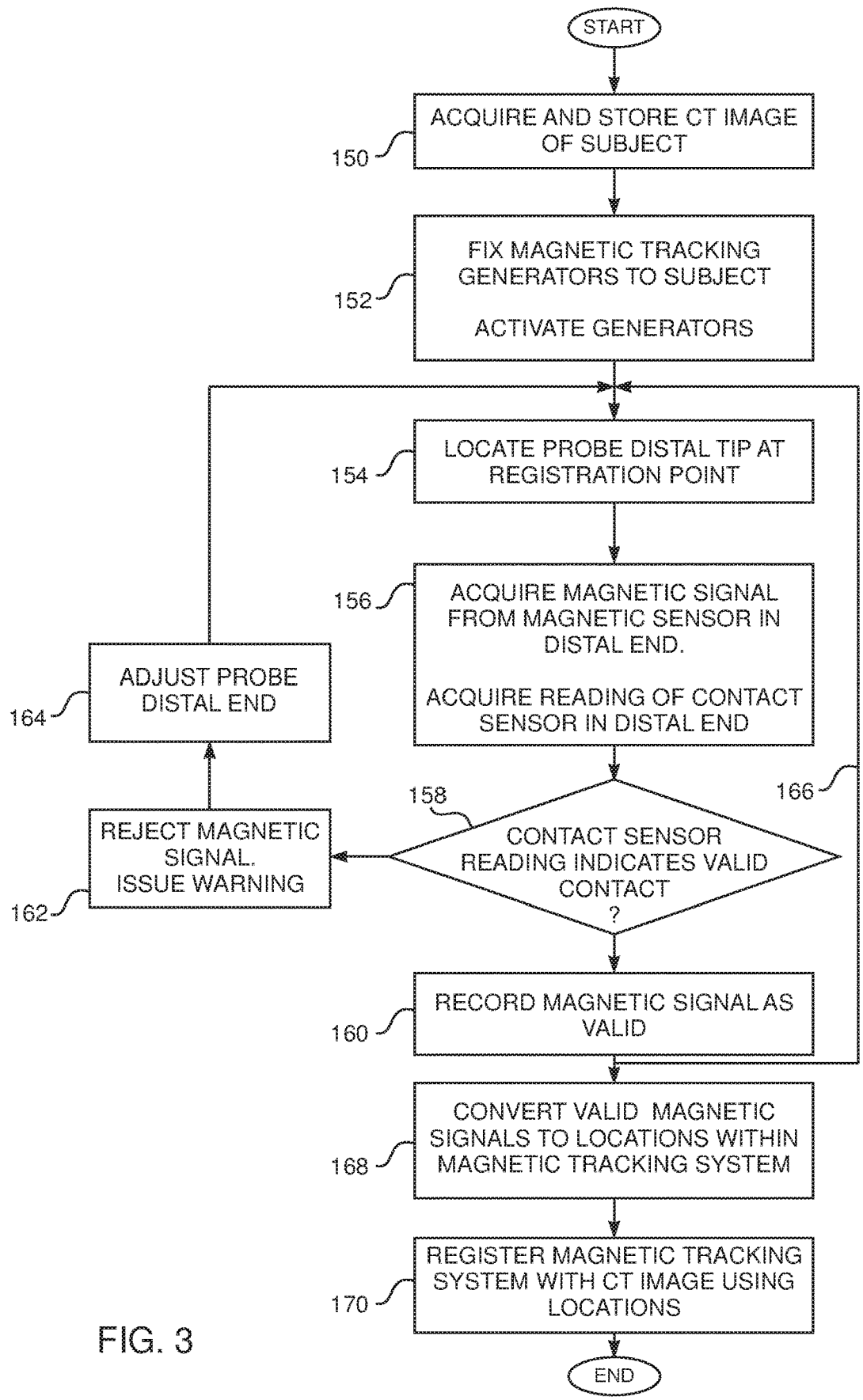
FIG. 3 is a flowchart of steps performed in operating the system, according to an embodiment of the present invention.

FIG. 1 is a schematic diagram of a surface registration system 10, according to an embodiment of the present invention. FIGS. 2A and 2B are schematic diagrams of probes, according to embodiments of the present invention. FIG. 3 is a flowchart of steps performed in operating system 10, according to an embodiment of the present invention. System 10 is used to register a magnetic tracking system 12 with an image, herein by way of example assumed to comprise a computerized tomography (CT) image, of a subject 14. Tracking system 12 is used to track positions and orientations of one or more instruments, such as catheters or guidewires, that are inserted into subject 14 during a medical procedure performed on the subject. As is described below, tracking system 12 is also able to track the position and orientation of a registration probe 28 that is external to the subject. Probe 28 is fixedly connected to a handle 32 that may be held by a professional 30 during use of system 10 (only the hand of the professional is shown in the figure). The combination of probe 28 and handle 32 form a rigid probe assembly 31 that facilitates the positioning by professional 30 of the probe to a desired location.

For clarity and simplicity in the following description, the medical procedure referred to above is assumed to comprise an invasive procedure on a nasal sinus of subject 14, so that surface registration system 10 and magnetic tracking system 12 are assumed to be configured to operate in and around the region of the nasal sinus. However, it will be understood that systems 10 and 12 may be configured to operate in and around other regions of a subject, such as the kidneys or abdomen, and those having ordinary skill in the art will be able to adapt the description herein for such other regions.

Tracking system 12 is operated by a system processor 16, comprising a processing unit 18 communicating with a probe tracking module 20. The function of module 20 is described below. Processor 16 may be mounted in a console 22, which comprises operating controls 24 that typically include a pointing device such as a mouse or trackball. As is indicated in the diagram, console 22 is grounded. Professional 30 uses the operating controls to interact with the processor, which, as described below, may be used to present results produced by systems 10 and 12 to the professional on a screen 34.

Processor 16 uses software stored in a memory of the processor to operate system 10. The software may be downloaded to processor 16 in electronic form, over a network, for example, or it may, alternatively or additionally, be provided and/or stored on non-transitory tangible media, such as magnetic, optical, or electronic memory.

In order to track the instruments referred to above within subject 14, as well as to track probe 28, processing unit 18 uses probe tracking module 20 to operate a plurality of magnetic field generators 40. In one embodiment, typically applicable if subject 14 is not anesthetized, generators 40, typically coils, are fixed to a frame 44 which is in turn clamped to a head 26 of subject 14, as illustrated in FIG. 1, and which is grounded. In an alternative embodiment, applicable if subject 14 is anesthetized and has a recumbent immobile head on a bed, the generators are fixed with respect to each other and to the head, typically by being placed on the bed, besides the subject's head, without using frame 44. In this case, a grounding patch 43 may be attached to the skin of subject 14.

The generators radiate alternating magnetic fields into and external to the head of the subject, and the fields generate signals in magnetic detectors in the instruments and in probe 28. The signals are conveyed back to processing unit 18 and module 20, typically in the case of probe 28 via a cable 50 connecting the probe to console 22, which analyze the signals to provide locations and orientations of the instruments and probe 28 with respect to generators 40. It will be understood that magnetic field generators 40 define a coordinate frame of reference 41 of magnetic tracking system 12.

The Carto® system, produced by Biosense Webster, of Diamond Bar, Calif., uses a tracking system similar to that described herein to track the location and orientation of the distal tip of a probe inserted into a subject.

As is described in more detail below, system processor 16 stores a digitized CT image 54 of head 26 of subject 14. The digitized CT image may be accessed by processing unit 18 for use in registration system 10, as well as to generate, inter alia, an image 58 of the subject's head on screen 34. During the process of registration, probe 28 is brought into contact with a surface 36 of subject 14, i.e., into contact with the skin of the subject, so that surface 36 is also referred to herein as skin 36.

FIG. 2A is a schematic diagram of a cross-section of probe 28, according to an embodiment of the present invention. Probe 28 comprises a magnetic detector 60, herein assumed to comprise one or more coils, which is located at a distal tip 64 of the probe and which generates a signal in response to the magnetic fields transmitted by generators 40. The signal is conveyed, typically by a signal conveying cable 68 which may comprise a conductive cable or alternatively a fiber optic cable, to the processing unit and probe tracking module of console 22. If cable 68 comprises a fiber optic cable, an electric signal produced in detector 60 may be converted to an optical signal for transmission in the fiber optic cable, using an optoelectronic transducer (not shown in the figure). Alternatively, the signal produced by detector 60 may be conveyed wirelessly to processing unit 42 and module 46. As described above, the processing unit uses the probe tracking module to determine from the signal the location and orientation of probe 28.

In addition to having detector 60 located at distal tip 64, the distal tip also comprises an electrode 72 which slightly protrudes from, or is flush with, an external surface 76 of the probe. If electrode 72 is configured to protrude from surface 76, the protrusion is typically approximately 100 microns. A conductive cable 80 connects electrode 72 to system console 22. Electrode 72 and cable 80 are isolated electrically from the ground of console 22, and as is described below, in this case the electrode acts as a contact sensor for probe 28 and is also referred to herein as contact sensor 72.

FIG. 2B is a schematic diagram of a cross-section of a probe 28A, according to an alternative embodiment of the present invention. Apart from the differences described below, the operation of probe 28A is generally similar to that of probe 28 (FIG. 2A), and elements indicated by the same reference numerals in both probes 28 and 28A are generally similar in construction and in operation. In contrast to probe 28, probe 28A does not comprise an electrode at its distal tip. Rather, a force sensor 90 is installed in the probe so that the force sensor is able to measure the force on distal tip 64. The force sensor may be any convenient force sensor known in the art, and may, for example, be a sensor similar to that provided in the Carto® system referred to above. Typically, force sensor 90 is configured to measure the magnitude and the direction of the force on the distal tip.

Signals from force sensor 90 may be conveyed wirelessly or by a cable 96, substantially as described above for signals from detector 60, to processing unit 18. The processing unit is configured to analyze the signals to provide a quantitative value for the force exerted on the distal tip of probe 28A.

FIG. 3 is a flowchart of steps performed in operating surface registration system 10, according to an embodiment of the present invention. The following description assumes, except where otherwise indicated, that probe 28 is used for the registration generated by the system, and also that frame 44 is attached to subject 14. Those having ordinary skill in the art will be able to adapt the description, as necessary, for the case wherein probe 28A is used, and/or when frame 44 is not used.

In an image acquisition step 150, system processor 16 acquires a tomographic image, herein assumed to comprise a CT image of the head of subject 14. The CT image is typically generated in a CT machine, and is then stored as digitized CT image 54 by the system processor. Step 150 is performed prior to the following steps of the flowchart, and typically may be performed a number of days prior to these steps.

In an installation step 152, frame 44 and its attached generators 40 are clamped to the head of subject 14. The generators are connected to console 22, and are activated by processing unit 18 using module 20. A portion of subject 14 is connected to ground. In one embodiment frame 44 is conductive and is grounded, so that clamping of the frame to the subject grounds the subject.

In a location step 154, professional 30 holds handle 32 and brings probe 28 into contact with one of a number of pre-determined registration points on the surface, i.e., the skin, of subject 14. There are typically approximately 3-4 registration points that are selected by professional 30, typically prior to implementation of the flowchart steps, and one of these is selected in step 154. The pre-determined points are typically geometrically well-defined points on the skin, such as the tip of the subject's nose, or the point on the subject's brow between the eyes. The pre-determined points are selected to be visible to the native eye of professional 30, and as well as being geometrically well-defined are selected to be on a part of the subject's skin that is immobile.

As probe 28 is brought into proximity with the subject's skin, detector 60 generates signals in response to the magnetic fields from generators 40 that traverse the detector.

In a signal acquisition step 156, the signals from detector 60 are received by processor 16. In addition the processor measures the impedance between electrode 72, also herein termed contact sensor 72, and ground by injecting an alternating current into the electrode. Contact sensor 72 and its connecting cable 80 are isolated from ground, so that while sensor 72 does not contact the skin of subject 14 the measured impedance is large, typically of the order of 10 MΩ or more. On contact with the subject's skin, the impedance reduces drastically.

The actual impedance between contact sensor 72 and ground depends on the "degree" or quality of contact of the sensor with the skin, as well as on the location and degree of contact of frame 44, or of grounding patch 43. For example, if the contact is extremely light the impedance may be approximately 100 kΩ. If, on the other hand, the contact is very strong, so that contact sensor 72 pushes into the skin of the subject, the impedance may drop to the order of 10 kΩ or less.

Embodiments of the present invention assign an acceptable range for the impedance between contact sensor 72 and ground. In one embodiment the acceptable range, using a frequency of 20 kHz, is 20 kΩ-40 kΩ. Below 20 kΩ the probe may depress the skin too much, by 1 mm or even more. Above 40 kΩ there may be no, or almost no, contact. In an alternative embodiment the acceptable range is determined by professional 30, without undue experimentation, and depends on the positioning and/or degree of contact of frame 44 and/or patch 43.

In the case of probe 28A, embodiments of the present invention use force sensor 90 as a contact sensor, so that force sensor 90 is also referred to herein as contact sensor 90. In step 156 the processor records the force registered by contact sensor 90. If sensor 90 does not contact the skin of subject 14, then the force registered by the sensor is zero. If the contact is strong so that sensor 90 pushes into the skin, then the force measured by the sensor is typically 10 gm or more.

Similarly to contact sensor 72 (the electrode), an acceptable range for the forces is assigned to the force measured by sensor 90. In one embodiment the acceptable range is 2 gm-8 gm. Below 2 gm there may be no, or almost no, contact; above 8 gm the probe may depress the skin too much. In an alternative embodiment the acceptable range for the forces is determined by professional 30, without undue experimentation, by the professional contacting with probe 28 selected points on the subject's skin.

In a decision step 158, processor 16 checks if the reading from the contact sensor, electrode 72 or force sensor 90, is within its acceptable range, indicating that probe 28 or probe 28A is making a valid contact with the skin of subject 14.

If step 158 returns a positive answer, then in a record signal step 160 the processor records the signal of step 156 from detector 60 as a valid signal. The processor may also provide a signal to professional 30, such as an auditory or visual signal, that the contact of the probe is a valid contact. An example of a visual signal in this case is positioning a green symbol at a corresponding location in image 58 on screen 34 (FIG. 1).

If step 158 returns a negative answer, then in a reject step 162 the processor does not record the signal of step 156, and typically issues an auditory and/or visual warning to professional 30 that acceptable contact has not been achieved. An example of a visual warning in this case is positioning a red symbol in image 58. In addition, the warning may provide an indication to the professional of how to adjust the probe distal end so as to realize acceptable contact. For example, if the contact sensor indicates that even though some contact has been made, the contact is too light, then the professional may be advised to increase the strength of the contact. If the sensor indicates the contact is too strong, the professional may be advised to reduce the contact strength.

In an adjustment step 164 the professional adjusts the probe to try to achieve acceptable contact, and the flowchart returns to step 154.

As indicated by line 166, as each magnetic signal is recorded as valid, the flowchart returns to step 154.

Once all the registration points have been processed in step 154 and their corresponding magnetic signals recorded as valid in step 160, in a conversion step 168 processor 16 converts the recorded magnetic signals to locations in a frame of reference defined by the magnetic tracking system, i.e., by generators 40 as attached to frame 44.

In a final step 170, the processor registers the values of the locations determined in step 168 with the corresponding location values of the CT image.

It will be understood that by following the process of the flowchart, processor 16 only records magnetic signals as valid when there is a valid contact with the skin of subject 14. If there is no valid contact, the processor does not record magnetic signal values.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Apparatus, comprising:
   a magnetic tracking system, which is configured to generate a magnetic field in a vicinity of a body of a living subject;
   a probe, having a distal end configured to be brought into contact with one or more registration points on a surface of the body, and comprising:
   a contact sensor, located within the distal end and configured to output first signals indicative of a quality of the contact between the distal end with the one or more registration points, wherein the contact sensor comprises an electrode; and
   a magnetic detector, located within the distal end and configured to output second signals in response to the magnetic field that are indicative of respective positions of the one or more respective registration points in a coordinate frame of the magnetic tracking system; and
   a processor configured to receive a tomographic image of the subject, and to verify, based on the quality of the contact indicated by the first signals, that the one or more registration points are valid, wherein verifying that the one or more registration points are valid comprises verifying that an impedance measured by the electrode on contact with each of the registration points lies within a predetermined range of 20 kΩ-40 kΩ when the impedance is measured at 20 kHz, and to register the tomographic image in the coordinate frame of the magnetic tracking system using the positions of the one or more registration points that were verified to be valid.

2. The apparatus according to claim 1, wherein the predetermined range is evaluated in response to a position of a grounding element on the surface of the body, and in response to a degree of contact of the grounding element with the surface.

3. The apparatus according to claim 1, and comprising a handle connected to the probe so as to form a rigid probe assembly.

4. The apparatus according to claim 1, wherein the one or more registration points are selected to be visible to a naked eye of a user of the probe.

5. The apparatus according to claim 1, wherein the one or more registration points are selected to be immobile on the surface of the body.

6. A method, comprising:
generating, with a magnetic tracking system, a magnetic field in a vicinity of a body of a living subject;
bringing a distal end of a probe into contact with one or more registration points on a surface of the body, the probe comprising:
a contact sensor, located within the distal end and configured to output first signals indicative of a quality of the contact between the distal end with the one or more registration points, wherein the contact sensor comprises an electrode, and
a magnetic detector, located within the distal end and configured to output second signals in response to the magnetic field that are indicative of respective positions of the one or more respective registration points in a coordinate frame of the magnetic tracking system;
receiving a tomographic image of the subject;
verifying, based on the quality of the contact indicated by the first signals, that the one or more registration points are valid, wherein verifying that the one or more registration points are valid comprises verifying that an impedance measured by the electrode on contact with each of the registration points lies within a predetermined range of 20 kΩ-40 kΩ when the impedance is measured at 20 kHz; and
registering the tomographic image in the coordinate frame of the magnetic tracking system using the positions of the one or more registration points that were verified to be valid.

7. The method according to claim 6, and comprising evaluating the predetermined range in response to a position of a grounding element on the surface of the body, and in response to a degree of contact of the grounding element with the surface.

8. The method according to claim 6, and comprising connecting a handle to the probe so as to form a rigid probe assembly.

9. The method according to claim 6, and comprising selecting the one or more registration points to be visible to a naked eye of a user of the probe.

10. The method according to claim 6, and comprising selecting the one or more registration points to be immobile on the surface of the body.

* * * * *